United States Patent
Leone et al.

(10) Patent No.: US 10,114,114 B2
(45) Date of Patent: *Oct. 30, 2018

(54) ULTRASONIC PROBE WITH PRECHARGE CIRCUIT AND METHOD OF CONTROLLING AN ULTRASONIC PROBE

(71) Applicant: STMicroelectronics S.r.l., Agrate Brianza (IT)

(72) Inventors: Antonio Davide Leone, Pieve Emanuele (IT); Davide Ugo Ghisu, Milan (IT); Fabio Quaglia, Pizzale (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,651

(22) Filed: Mar. 26, 2015

(65) Prior Publication Data

US 2016/0077198 A1 Mar. 17, 2016

(30) Foreign Application Priority Data

Sep. 15, 2014 (IT) .............................. TO2014A0729

(51) Int. Cl.
  *G01S 7/52* (2006.01)
  *G01N 29/36* (2006.01)
  (Continued)

(52) U.S. Cl.
  CPC .......... *G01S 7/52023* (2013.01); *G01N 29/34* (2013.01); *G01N 29/36* (2013.01);
  (Continued)

(58) Field of Classification Search
  CPC .... G01S 7/52033; G01N 29/36; G01N 29/34; G01N 2291/106; H03F 1/301; H03F 3/70; H03F 2200/453; H03F 2200/456
  (Continued)

(56) References Cited

U.S. PATENT DOCUMENTS

| 4,274,056 A | 6/1981 | Lukes et al. |
| 4,918,341 A | 4/1990 | Galbraith et al. |

(Continued)

FOREIGN PATENT DOCUMENTS

| CN | 102668380 A | 9/2012 |
| CN | 205092962 U | 3/2016 |

(Continued)

OTHER PUBLICATIONS

Gurun et al., "Front-End Receiver Electronics for High-Frequency Monolithic CMUT-on-CMOS Imaging Arrays," *IEEE Transaction on Ultrasonics, Ferroelectrics, and Frequency Control* 58(8):1658-1669, 2011.

(Continued)

*Primary Examiner* — Edwin Holloway, III
(74) *Attorney, Agent, or Firm* — Seed IP Law Group LLP

(57) ABSTRACT

An ultrasonic probe includes: an ultrasonic transducer; an amplification stage; a bias circuit, which determines a bias voltage on an input terminal of the amplification stage; and a selector having an intermediate node, a high-voltage switch between the intermediate node and the transducer, and a first low-voltage switch between the intermediate node and the input terminal. A control unit controls the high-voltage switch and the first low-voltage switch so as to alternately couple and decouple the amplification stage and the transducer. A precharge circuit determines a precharge voltage on the intermediate node as a function of the bias voltage, before the amplification stage and the transducer are coupled.

28 Claims, 5 Drawing Sheets

(51) Int. Cl.
  *H03F 1/30* (2006.01)
  *H03F 3/70* (2006.01)
  *G01N 29/34* (2006.01)

(52) U.S. Cl.
  CPC .............. *H03F 1/301* (2013.01); *H03F 3/70* (2013.01); *G01N 2291/106* (2013.01); *H03F 2200/453* (2013.01); *H03F 2200/456* (2013.01)

(58) Field of Classification Search
  USPC ......................................................... 367/197
  See application file for complete search history.

(56) References Cited

U.S. PATENT DOCUMENTS

| | | | |
|---|---|---|---|
| 5,832,923 A * | 11/1998 | Engeler | G01S 7/52046 600/459 |
| 6,677,807 B1 | 1/2004 | Brokaw | |
| 7,967,754 B2 | 6/2011 | Knight | |
| 8,488,812 B2 | 7/2013 | David et al. | |
| 2005/0154300 A1* | 7/2005 | Wodnicki | H04B 11/00 600/437 |
| 2006/0061231 A1* | 3/2006 | Kameishi | G01S 7/52025 310/314 |
| 2010/0237807 A1* | 9/2010 | Lemmerhirt | G01H 11/06 318/116 |
| 2013/0265855 A1 | 10/2013 | Ghisu et al. | |
| 2014/0159702 A1 | 6/2014 | Doege | |
| 2014/0288428 A1* | 9/2014 | Rothberg | A61B 8/145 600/447 |
| 2015/0091646 A1* | 4/2015 | Shifrin | H03F 3/21 330/255 |

FOREIGN PATENT DOCUMENTS

| | | |
|---|---|---|
| DE | 3618222 A1 | 12/1987 |
| DE | 10 2012 014 197 A1 | 1/2014 |

OTHER PUBLICATIONS

Italian Search Report and Written Opinion, dated Jun. 11, 2015, for corresponding IT Application No. TO20140729, 8 pages.
Palmisano et al., "A Replica Biasing for Constant-Gain CMOS Open-Loop Amplifiers," IEEE International Symposium on Circuits and Systems, May 31-Jun. 3, 1998, Monterey, CA, pp. 363-366.
Peng et al., "A Charge-Based Low-Power High-SNR Capacitive Sensing Interface Circuit," *IEEE Transactions on Circuits and Systems—I: Regular Papers* 55(7):1863-1873, 2008.
Savoia et al., "An Ultra-Low-Power Fully Integrated Ultrasound Imaging CMUT Transceiver Featuring a High-Voltage Unipolar Pulser and a Low-Noise Charge Amplifier," IEEE International Ultrasonics Symposium (IUS), Sep. 3-6, 2014, Chicago, IL, pp. 2568-2571.
Zhao et al., "High-voltage Pulser for Ultrasound Medical Imaging Applications," 13th International Symposium on Integrated Circuits (ISIC), Dec. 12-14, 2011, Singapore, SG, pp. 408-411.
Chinese Search Report, dated Apr. 24, 2017, for Chinese Application No. 2015105838819, 2 pages.
Sautto et al., "A CMUT Transceiver Front-End with 100-V TX Driver and 1-mW Low-Noise Capacitive Feedback RX Amplifier in BCD-SOI Technology," *40th European Solid State Circuits Conference (ESSCIRC)*, ESSCIRC 2014, Venice Lido, Sep. 22-26, 2014, pp. 407-410.
Yamaner et al., "Front-end IC Design for Intravascular Ultrasound Imaging," *Ph.D. Research in Microelectronics and Electronics*, Istanbul, Jun. 22, 2008, pp. 257-260.

* cited by examiner

ULTRASONIC PROBE WITH PRECHARGE CIRCUIT AND METHOD OF CONTROLLING AN ULTRASONIC PROBE

BACKGROUND

Technical Field

The present disclosure relates to ultrasonic probes and to methods of controlling ultrasonic probes.

Description of the Related Art

As is known, ultrasonic probes find widespread use in various sectors, amongst which also that of imaging diagnostics, where they are used in ultrasonographic scanners or ultrasonic tomography scanners.

An ultrasonic probe, for example, but not exclusively, for ultrasonography or ultrasonic tomography in general comprises an array of transducers housed in a package together with respective excitation and read circuits, which are governed by a control unit.

The transducers are configured to convert pressure waves into electrical signals and vice versa and may, for example, be piezoelectric transducers or else membrane capacitive transducers.

The excitation and read circuits are alternately connected to the transducers for generating ultrasound pulse trains (for example, at a frequency comprised between 2 MHz and 20 MHz) during a transmitting step and receiving return echoes, caused by variations of acoustic impedance in the medium in which the pulses are transmitted, during a receiving step.

Switching between the transmitting configuration and the receiving configuration is controlled both because the read circuits, at low voltage, have to be continuously protected from the high voltages (even higher than 100 V) used by transmission circuits and because disturbance may occur and reception of the return echoes may be jeopardized. Switching should further be fast, also to enable sonographic investigation in the near field, e.g., in the more superficial portion of the tissue or other body being examined. The return echoes, in fact, may not be correctly received if the read circuits and the transducers are not stably biased.

The problems linked to switching between the transmitting configuration and the receiving configuration are particularly felt for arrays in which each transducer has a single respective terminal accessible individually, whereas a further terminal is in common with corresponding terminals of the other transducers. On the other hand, both for reasons of costs of production of the transducers and on account of their smaller overall dimensions, probes of this type are better suited to integration and are normally preferred to probes in which the transducers have both of the terminals accessible individually.

BRIEF SUMMARY

In an embodiment, an ultrasonic probe comprises: an ultrasonic transducer; an amplification stage; a first bias circuit configured to determine a bias voltage on an input terminal of the amplification stage; a selector having an intermediate node, a high-voltage switch between the intermediate node and the transducer, and a first low-voltage switch between the intermediate node and the input terminal of the amplification stage; a control unit configured to control the high-voltage switch and the first low-voltage switch so as to alternately couple and decouple the amplification stage and the transducer; and a precharge circuit configured to determine a precharge voltage on the intermediate node as a function of the bias voltage before the amplification stage and the transducer are coupled by the control unit. In an embodiment, the first bias circuit comprises a bias generator configured to supply a bias current and the amplification stage is configured to present the bias voltage on the input terminal in response to the bias current. In an embodment, the precharge circuit comprises: a second bias circuit configured to supply a precharge current in a precharge relation with the bias current; and a copy stage, configured to determine the second bias voltage on the intermediate node when the bias current and the precharge current are in the precharge relation. In an embodiment, the second bias circuit comprises a precharge generator controlled to supply the precharge current as a function of the bias current. In an embodiment, the precharge generator is fitted into current-mirror configuration to the bias generator. In an embodiment, the precharge current and the bias current are in a mirror ratio; the amplification stage comprises a first transistor, which is coupled to the first bias circuit to receive the bias current and has a control terminal coupled to the input terminal and a first aspect ratio; the copy stage comprises a second transistor, which is coupled to the second bias circuit to receive the precharge current at least in an operating configuration and has a control terminal coupled to the intermediate node and a second aspect ratio; and the second aspect ratio is a multiple of the aspect ratio of the transistor that is equal to the mirror ratio. In an embodiment, the mirror ratio is not a unit ratio. In an embodiment, the amplification stage and the copy stage are of the single-transistor type. In an embodiment, the second bias circuit is selectively activatable by the control unit for a precharge time interval, before the amplification stage and the transducer are coupled by the control unit. In an embodiment, the selector comprises a second low-voltage switch between the intermediate node and ground, and the control unit is configured to simultaneously close the first low-voltage switch and opening the second low-voltage switch when the control unit couples the amplification stage and the transducer. In an embodiment, the second bias voltage on the intermediate node is substantially equal to the first bias voltage. In an embodiment, the amplification stage is in charge-amplifier configuration. In an embodiment, the ultrasonic probe comprising a further selector, having a structure identical to that of the selector, and an impedance-matching stage, having its impedance correlated to a capacitance of the transducer and to an impedance upstream of the selector, wherein the amplification stage is of a differential type and has a further input terminal which are selectively connectable to the impedance-matching stage through the further selector.

In an embodiment, a method comprises: controlling a selector having an intermediate node, a high-voltage switch between the intermediate node and an ultrasonic transducer, and a low-voltage switch between the intermediate node and an input terminal of an amplification stage so as to alternately couple and decouple the transducer and the amplification stage; and precharging the intermediate node as a function of a bias voltage on the input terminal of the amplification stage before coupling the amplification stage and the transducer. In an embodiment, the precharging comprises bringing the intermediate node to a precharge voltage substantially equal to the bias voltage. In an embodiment, the coupling comprises closing the low-voltage switch.

In an embodiment, a device comprises: a low-voltage amplifier including an amplifier input and amplifier biasing circuitry configured to bias the amplifier; and a selection circuit configured to couple between the amplifier input and an ultrasonic transducer and including: a node; a first switch coupled between the node and the amplifier input; and node biasing circuitry coupled to the amplifier biasing circuitry and configured to, before the first switch couples the node to the amplifier input in a receive mode of operation, bias the node based on the biasing of the amplifier. In an embodiment, the amplifier-input biasing circuitry comprises a first current source, the node biasing circuitry comprises a second current source, and the first current source and the second current source are coupled together in a current-mirror configuration having a current mirror ratio. In an embodiment, the selection circuitry comprises: a second switch coupled between the second current source and the node; and at least one transistor having a control terminal coupled to the node and conduction terminals configured to couple between the node and a reference voltage terminal. In an embodiment, the device comprises a high-voltage switch configured to couple between the node and the ultrasonic transducer. In an embodiment, the device comprises a diode coupled between the node and a reference voltage. In an embodiment, the device comprises a controller configured to control operation of the first, second and high-voltage switches. In an embodiment, the controller is configured to control the second switch and the high voltage switch to, in operation, couple the second current source to the node for a pre-charge period before coupling the ultrasonic transducer to the node. In an embodiment, the device comprises a third switch coupled between a conduction terminal of the at least one transistor and a reference voltage terminal, wherein the controller is configured to, in operation, control the first and third switches to simultaneously disconnect the conduction terminal of the at least one transistor from the reference voltage terminal and couple the node to the amplifier input. In an embodiment, the amplifier comprises at least one first transistor having: a conduction terminal coupled to the first current source; a control terminal coupled to the amplifier input; and a first aspect ratio; and the selection circuit comprises at least one second transistor having: a conduction terminal configured to couple to the second current source; a control terminal coupled to the node; and a second aspect ratio, where the second aspect ratio is a multiple of the first aspect ratio and the multiple is based on the current mirror ratio. In an embodiment, the current mirror ratio is greater than 1. In an embodiment, the node biasing circuitry is configured to, before the first switch couples the node to the amplifier input in the receive mode of operation, bias the node to a bias voltage substantial equal to a biasing voltage of the amplifier. In an embodiment, the amplifier has a charge amplifier configuration. In an embodiment, the amplifier has a differential amplifier configuration having a second amplifier input, and the device comprises: a second selection circuit configured to couple between the second amplifier input and an impedance representative of an impedance of the ultrasonic transducer and including: a second node; a switch coupled between the second node and the second amplifier input; and second node biasing circuitry coupled to the amplifier biasing circuitry and configured to, before the switch coupled between the second node and the second amplifier input couples the second node to the second amplifier input in the receive mode of operation, bias the second node based on the biasing of the amplifier.

In an embodiment, a system comprises: an ultrasonic transducer; a low-voltage amplifier including an amplifier input and amplifier biasing circuitry configured to bias the amplifier; and a selection circuit configured to couple between the amplifier input and the ultrasonic transducer, and including: a node; a first switch coupled between the node and the amplifier input; and node biasing circuitry coupled to the amplifier biasing circuitry and configured to, before the first switch couples the node to the amplifier input in a receive mode of operation, bias the node based on the biasing of the amplifier. In an embodiment, the amplifier-input biasing circuitry comprises a first current source, the node biasing circuitry comprises a second current source, and the first current source and the second current source are coupled together in a current-mirror configuration having a current mirror ratio. In an embodiment, the selection circuit comprises: a second switch coupled between the second current source and the node; and at least one transistor having a control terminal coupled to the node and conduction terminals configured to couple between the node and a reference voltage terminal. In an embodiment, the system comprises a high-voltage switch configured to couple between the node and the ultrasonic transducer. In an embodiment, the system comprises a controller configured to control operation of the first, second and high-voltage switches. In an embodiment, the amplifier has a differential amplifier configuration having a second amplifier input, and the system comprises: a second selection circuit configured to couple between the second amplifier input and an impedance representative of an impedance of the ultrasonic transducer and including: a second node; a switch coupled between the second node and the second amplifier input; and second node biasing circuitry coupled to the amplifier biasing circuitry and configured to, before the switch coupled between the second node and the second amplifier input couples the second node to the second amplifier input in the receive mode of operation, bias the second node based on the biasing of the amplifier.

In an embodiment, a method comprises: controlling a selector, the selector having an intermediate node, a high-voltage switch coupled between the intermediate node and an ultrasonic transducer, and a low-voltage switch coupled between the intermediate node and an input terminal of an amplification stage of an ultrasonic probe, to alternately couple and decouple the transducer and the amplification stage; and precharging the intermediate node as a function of a bias voltage on the input terminal of the amplification stage before coupling the amplification stage and the transducer. In an embodiment, the precharging comprises bringing the intermediate node to a precharge voltage substantially equal to the bias voltage. In an embodiment, the method comprises starting the precharging before coupling the transducer to the intermediate node. In an embodiment, the method comprises simultaneously: decoupling the intermediate node from a reference voltage terminal; and coupling the intermediate node to the input terminal of the amplification stage.

In an embodiment, a non-transitory computer-readable medium's contents configure a system to perform a method, the method comprising: controlling a selector, the selector having an intermediate node, a high-voltage switch coupled between the intermediate node and an ultrasonic transducer, and a low-voltage switch coupled between the intermediate node and an input terminal of an amplification stage of an ultrasonic probe, to alternately couple and decouple the transducer and the amplification stage; and precharging the intermediate node as a function of a bias voltage on the input terminal of the amplification stage before coupling the amplification stage and the transducer. In an embodiment, the precharging comprises bringing the intermediate node to a precharge voltage substantially equal to the bias voltage. In an embodiment, the method comprises starting the precharging before coupling the transducer to the intermediate node.

In an embodiment, the method comprises simultaneously: decoupling the intermediate node from a reference voltage terminal; and coupling the intermediate node to the input terminal of the amplification stage.

BRIEF DESCRIPTION OF THE SEVERAL VIEWS OF THE DRAWINGS

For a better understanding of the disclosure, an embodiment thereof will now be described, purely by way of non-limiting example and with reference to the attached drawings, wherein.

DETAILED DESCRIPTION

Figure 1:
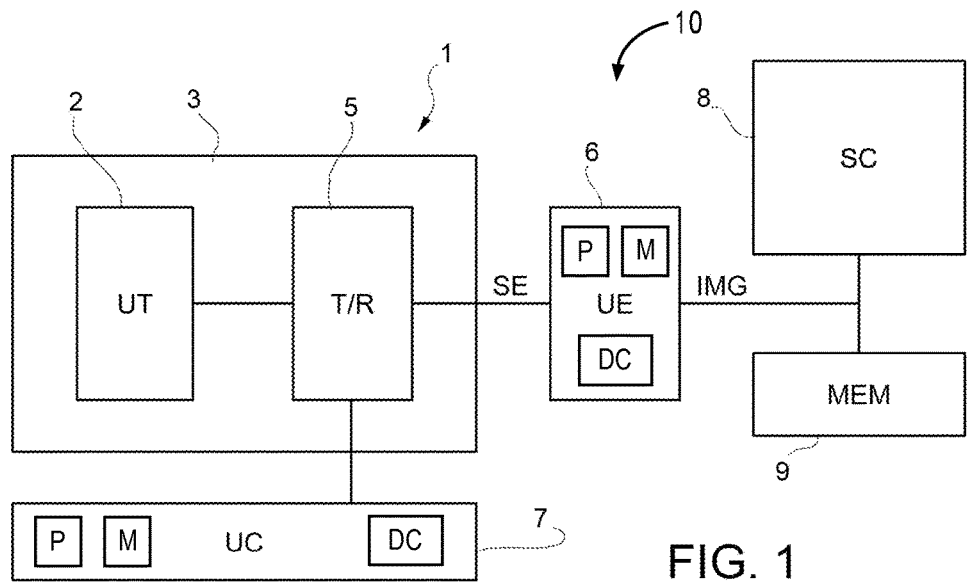
FIG. 1 is a simplified block diagram of a sonographic apparatus.

In FIG. 1, an ultrasonic probe for ultrasonography or ultrasonic tomography is illustrated schematically and designated as a whole by the reference number 1. The probe 1 comprises an array of ultrasonic transducers 2, housed in a package 3, transmission and receiver circuits 5, and a control unit 7. The transducers 2 and the transmission and receiver circuits 5 may be integrated in a same chip or, alternatively, provided in distinct chips. As illustrated, the transmission and receiver circuits 5 are housed within the package 3. The transmission and receiver circuits 5 are coupled to a processing unit 6 for supplying echo signals SE indicating return echoes captured by the transducers 2. The processing unit 6 receives and processes the echo signals SE for generating sonographic images IMG that may be displayed on a screen 8 and/or stored in a mass memory 9. As illustrated, the control unit 7 and the processing unit 6 comprise one or more processors P, one or more memories M, and discrete circuitry DC, which may be configured alone or in various combinations to provide the functionality of the control unit 7 and the processing unit 6.

The probe 1, the processing unit 6, the screen 8, and the mass memory 9 form an ultrasonographic scanner or ultrasonic tomography scanner 10.

Figure 2:
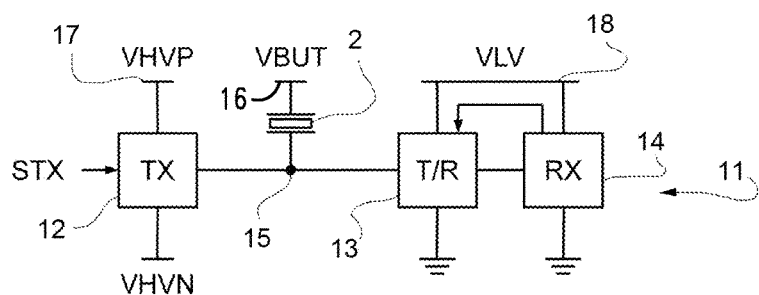
FIG. 2 is a more detailed block diagram of an ultrasonic probe according to an embodiment, incorporated in the sonographic apparatus of FIG. 1.
Figure 2:
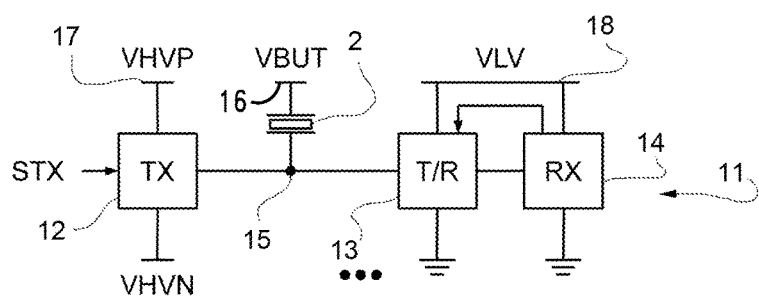
Figure 2:
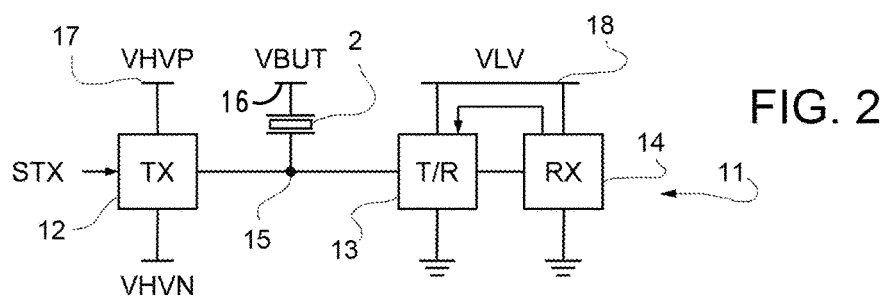

As illustrated in FIG. 2, the transducers 2 and the transmission and receiver circuits (5 in FIG. 1) are organized for forming a plurality of transmit/receive channels 11, each of which comprises a transducer 2, a pulse generator 12, a transmit/receive (or T/R) selector 13, and a receiver circuit 14. In a different embodiment (not illustrated), one or more pulse generators 12 and receiver circuits 14 may be shared, for example, in time sharing by a multiplexer, among a number of transducers 2.

In each channel 11, the transducer 2 has a respective first terminal coupled to a respective transmit/receive (or T/R) node 15 and a second terminal coupled to a reference node 16 common to the transducers 2 of all the channels 11 and set at a bias voltage VBUT.

Figure 3:
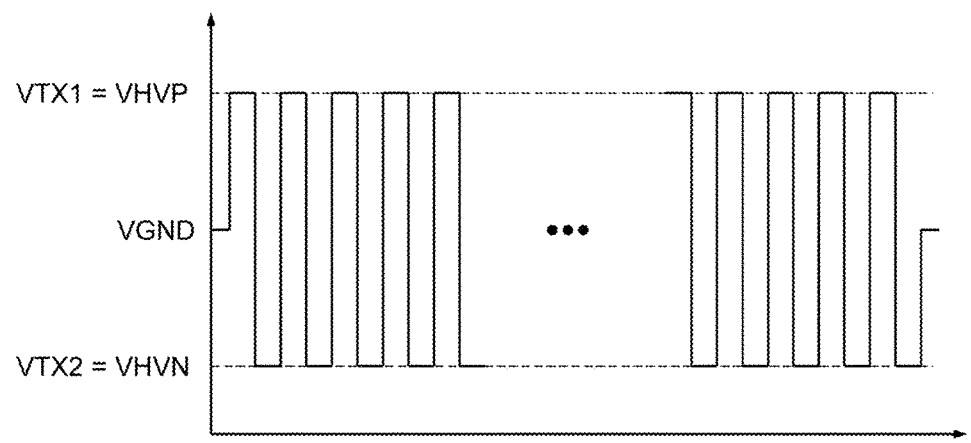
FIG. 3 is a graph representing physical quantities for the ultrasonic probe of FIG. 2.

The pulse generator 12 has an output terminal coupled to the T/R node 15 and is activated by the control unit 7 (see FIG. 1) by a transmission control signal STX in a transmitting configuration, and deactivated otherwise. When activated, the pulse generator 12 supplies to the T/R node 15 a sequence of pulses at high voltage and at a frequency comprised, for example, between 2 MHz and 20 MHz, causing oscillation of its output between a first transmission voltage VTX1 and a second transmission voltage VTX2, as illustrated in FIG. 3. In one embodiment, the first transmission voltage VTX1 may be a supply voltage VHVP (positive high voltage), supplied by a supply line 17a and comprised, for example, between 100 V and 200 V, and the second transmission voltage VTX2 may be a supply voltage VHVN (negative high voltage), supplied by a supply line 17b and comprised, for example, between −100 V and −200 V, or else a reference voltage, for example a ground voltage (VGND=0 V). Other waveforms may be employed.

The T/R selector 13 is arranged between the T/R node 15 and the receiver circuit 14 and is controlled by the control unit 7 so as to alternately couple the receiver circuit 14 to the T/R node 15 in a receiving configuration and decouple the receiver circuit 14 and the T/R node 15 otherwise, and in any case at least in the transmitting configuration. The T/R selector 13 and the receiver circuit 14 are further coupled to a second supply line 18, which supplies a supply voltage VLV (low voltage), lower than the supply voltage VHVP and comprised, for example, between 1 V and 3 V. In the receiving configuration, the receiver circuit 14 detects the electrical signals generated by the transducer 2 in response to pressure waves caused by return echoes, and supplies respective echo signals SE.

Figure 4:
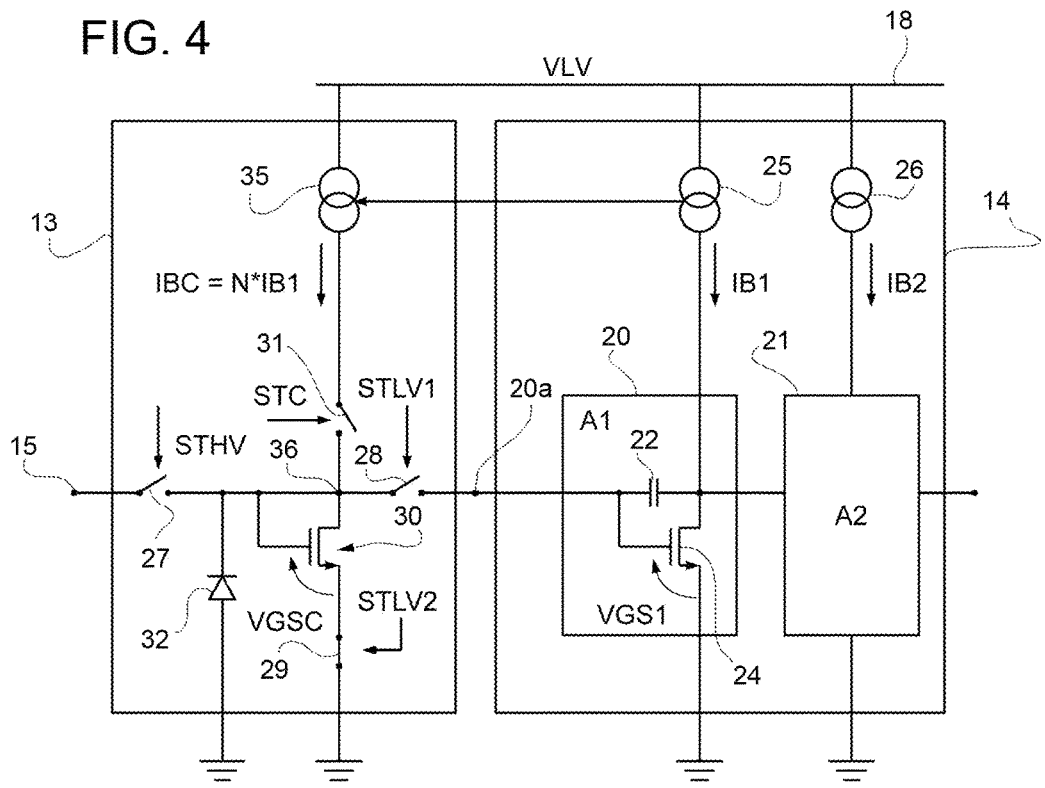
FIG. 4 is a more detailed block diagram of components of the ultrasonic probe of FIG. 2 in a first operating configuration.

FIG. 4 shows in greater detail, for one of the channels 11, the transducer 2, the T/R selector 13, and the receiver circuit 14.

In particular, the receiver circuit 14 comprises an input amplification stage 20, which has an input terminal 20a coupled to the T/R selector 13, which also defines an input of the receiver circuit 14, as well as possible further amplification stages 21. The input amplification stage 20 and the amplification stages 21 form a low-noise amplifier (LNA).

In an embodiment, the input amplification stage 20 is a single-terminal stage in a charge-amplifier configuration, with a capacitor 22 between the input and the output. More specifically, in the example illustrated in FIG. 4 the input amplification stage is of the single-transistor type, for reducing noise, and comprises an NMOS transistor 24 having its gate terminal coupled to the input terminal 20a, its source terminal connected to ground, and its drain terminal coupled to a first bias generator 25, which supplies a first bias current IB1. The input amplification stage 20 may provide a first gain component A1. In one embodiment (not illustrated), the amplification stage is of a differential type and receives a reference voltage at an input.

The amplification stages 21, which are optional, use a second bias current IB2 supplied by a second bias generator 26 and may provide a gain component A2.

The T/R selector 13 comprises a high-voltage switch 27, a first low-voltage switch 28, a second low-voltage switch 29, a copy stage 30, a precharge switch 31, and a diode 32. Furthermore, a precharge generator 35 supplies to the T/R selector 13 a precharge current IBC as a function of the first bias current IB1 and according to the operating conditions. In one embodiment, the precharge generator 35 is controlled by the first bias generator 25 in such a way that between the precharge current IBC and the first bias current IB1 there is a precharge relation. For instance, the precharge generator 35 and the first bias generator 25 form a current-mirror circuit, with not necessarily unit mirror ratio N. The precharge generator 35, the precharge switch 31, and the copy stage 30 form a precharge circuit that imposes a bias voltage on the common node 36 as a function of the voltage on the input node 20a of the input amplification stage 20, as described in detail hereinafter.

The high-voltage switch 27 may comprise a high-voltage MOS transistor; the first low-voltage switch 28, the second low-voltage switch 29, and the precharge switch 31 may comprise respective low-voltage MOS transistors.

In greater detail, the high-voltage switch 27 has its conduction terminals coupled to the T/R node 15 and to an intermediate node 36, respectively. The first low-voltage switch 28 has its conduction terminals coupled to the intermediate node 36 and to the input terminal 20a of the first input amplification stage 20, respectively. The high-voltage switch 27 and the first low-voltage switch 28 thus enable coupling and decoupling alternately of the T/R node 15 and the input amplification stage 20.

The second low-voltage switch 29 and the copy stage 30 are arranged in series between the intermediate node 36 and ground.

The precharge switch 31 is arranged between the precharge generator 35 and the intermediate node 36.

The diode 32 has its anode terminal connected to ground and its cathode terminal connected to the intermediate node 36, and limits the voltage variations of the intermediate node 36 due to capacitive couplings in the case of bipolar pulses.

The copy stage 30 has a structure substantially similar to that of the input amplification stage 20, but for a scale factor. In particular, the copy stage 30 is configured in such a way that a control voltage VGSC of the copy stage 30 is substantially equal to a control voltage VGS1 of the input amplification stage 20 when the first bias current IB1 of the input amplification stage 20 and the precharge current IBC of the copy stage 30 are in the precharge relation with one another. In one embodiment, the copy stage 30 comprises an NMOS transistor in diode configuration, having its source terminal connected to ground through the second low-voltage switch 29, whereas its drain and gate terminals are both coupled to the intermediate node 36. The NMOS transistor forming the copy stage 30 has an aspect ratio $(W/L)_C$ that is a multiple of the aspect ratio $(W/L)_1$ of the NMOS transistor 24 equal to the mirror ratio N between the precharge current IBC of the copy stage 30 and the first bias current IB1 of the input amplification stage 20. Alternatively, the copy stage 30 may comprise N NMOS transistors substantially identical to the NMOS transistor 24 and connected together in parallel, N again being the mirror ratio between the precharge current IBC of the copy stage 30 and the first bias current IB1.

The high-voltage switch 27, the first low-voltage switch 28, the second low-voltage switch 29, and the precharge switch 31 are controlled by the control unit 7 by a high-voltage timing signal STHV, a first low-voltage timing signal STLV1, a second low-voltage timing signal STLV2, and a precharge timing signal STC, respectively.

In a transmitting configuration (FIG. 4), the high-voltage switch 27 is open for insulating the input amplification stage 20 from the high voltages (100-200 V) supplied by the pulse generator 12 to the transducer 2. The second low-voltage switch 29 is instead closed for connecting the source terminal of the NMOS transistor that forms the copy stage 30 to ground.

Figure 5:
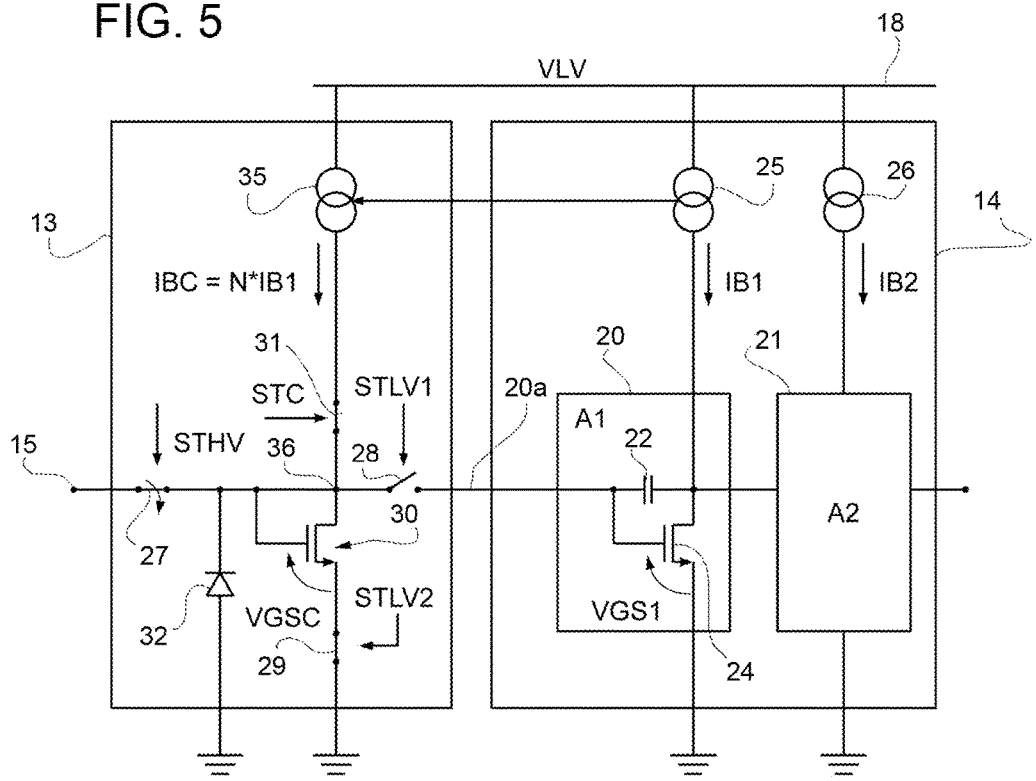
FIG. 5 is a block diagram that shows the components of FIG. 4 during a transition between the first operating configuration and a second operating configuration.
Figure 6:
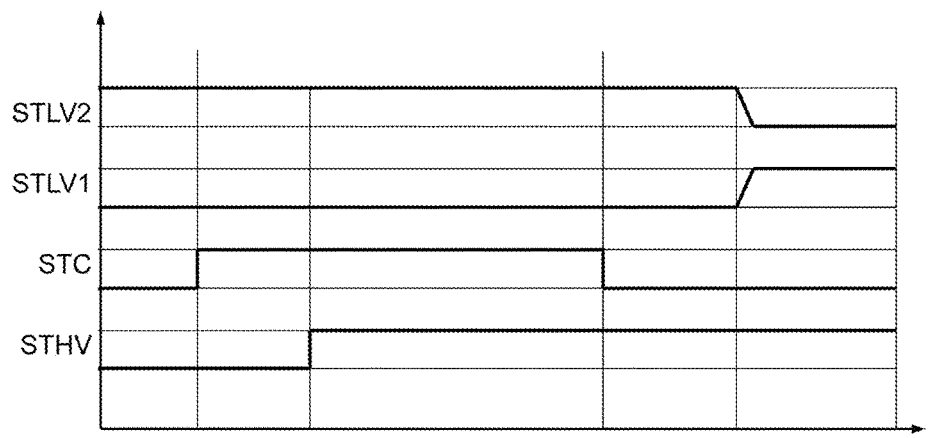
FIG. 6 is a graph that shows timing signals used for actuation of the probe of FIG. 2.
Figure 7:
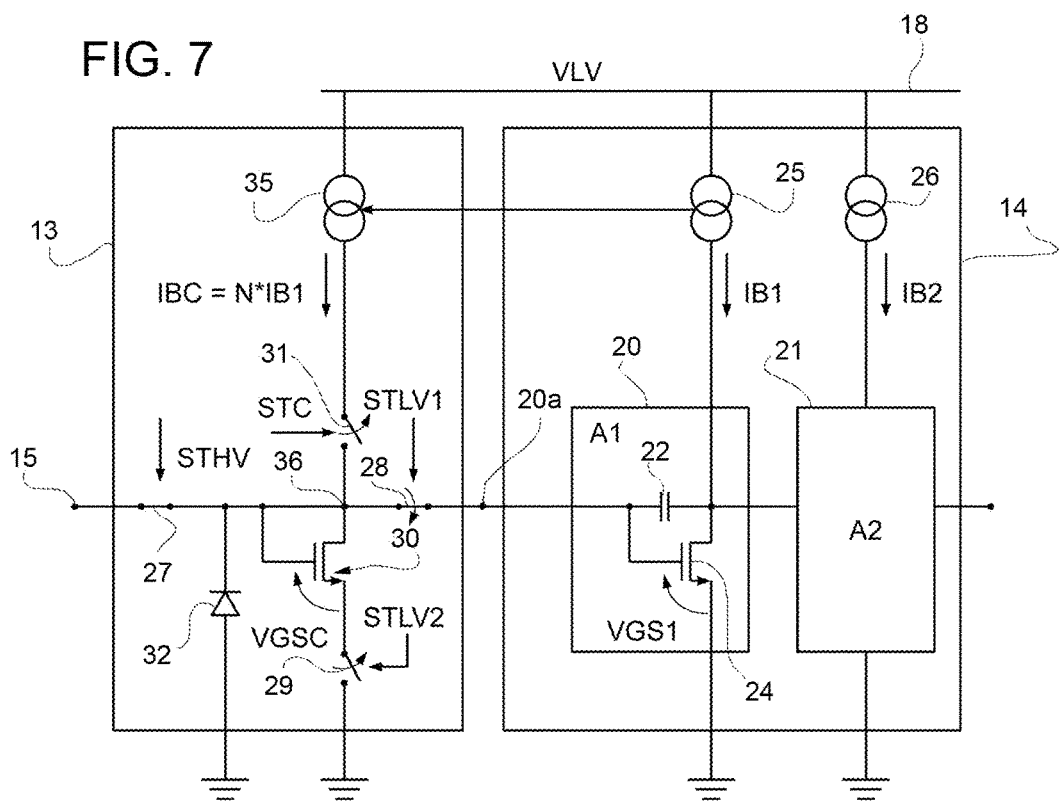
FIG. 7 is a block diagram that shows the components of FIG. 4 in the second operating configuration.

The pulse generator 12 supplies a train of pulses of a duration that is programmed or controlled by the control unit 7. At the end of each pulse train, the control unit 7 deactivates the pulse generator 12 and sets the probe 1 in the receiving configuration. In the first place, the control unit 7 closes the high-voltage switch 27 (FIG. 5; see also FIG. 7, where it is assumed by convention that low values of the timing signals STHV, STLV1, STLV2, STC correspond to an open state of the respective switches 27, 28, 29, 31 and high values correspond to a closed state). While the low-voltage switches 28, 29 are still in the transmitting configuration, the precharge switch 31 is closed, thus connecting the precharge generator 35 to the copy stage 30. In this way, the precharge current IBC is forced through the copy stage 30 and imposes a value of the control voltage VGSC equal to the value of the control voltage VGS1 of the input amplification stage 20. The precharge current IBC and the first bias current IB1 are in fact in the precharge relation, irrespective of possible fluctuations of the first bias current IB1, thanks to the fact that the precharge generator 35 is controlled by the first bias generator 25. The precharge switch 31 is kept closed for a precharge time interval ΔT sufficient to enable the control voltage VGSC of the NMOS transistor that forms the copy stage 30 and, consequently, the voltage on the intermediate node 36 to stably set at the value of the control voltage VGS1 of the input amplification stage 20. The duration of the precharge time interval ΔT depends upon the precharge current IBC. The step of precharging the intermediate node 36 may start even before the high-voltage switch 27 is closed. Consequently, according to the design choices (e.g., in practice according to the precharge relation between the precharge current IBC and the first bias current IB1), the precharge switch 31 could be closed while the high-voltage switch 27 is still open, as in the example of FIGS. 5 and 6.

Once the precharge time interval ΔT has elapsed, the first low-voltage switch 28 and the second low-voltage switch 29 are switched simultaneously. Switching is carried out in such a way as to cause a process of charge sharing between the second low-voltage switch 29, which is initially closed and is then opened, and the first low-voltage switch 28, which is initially open and is then closed. Possibly, taking the sizing of the components into consideration, also the precharge switch 31 may be opened simultaneously with switching of the first low-voltage switch 28 and second low-voltage switch 29 to be involved in the process of charge sharing. In particular, the charge initially stored for forming the channel of the second low-voltage switch 29 (MOS transistor that turns off) is released and comes to form the channel of the first low-voltage switch 28 (MOS transistor that enters into conduction). In this way, the charge injection into the input amplification stage 20 is minimized, thus reducing the sensitivity to noise and without delaying switching of the T/R selector 13 as a whole. Charge sharing is obtained by driving the control terminals of the low-voltage switches 28, 29 for obtaining a slow transition, represented in an exaggerated way in FIG. 6. In other words, applied to the control terminals of the low-voltage switches 28, 29 are ramp voltages of the duration of some nanoseconds instead of substantially step-like voltages (in practice, of the duration of tens or hundreds of picoseconds).

The precharge of the intermediate node 36 of the T/R selector 13 described facilitates bringing the probe 1 from the transmitting configuration to the receiving configuration in a very short time. In fact, the precharge current IBC charges the capacitances associated to the intermediate node 36 up to the appropriate level for receiving the pressure waves correctly by the transducer 2 already prior to closing of the first low-voltage switch 28. As soon as transition of the first low-voltage switch 28 is completed, the probe 1 is already in a condition to detect the echoes reflected, and it is thus possible to extend the sonographic investigation also to the near field.

Figure 8:
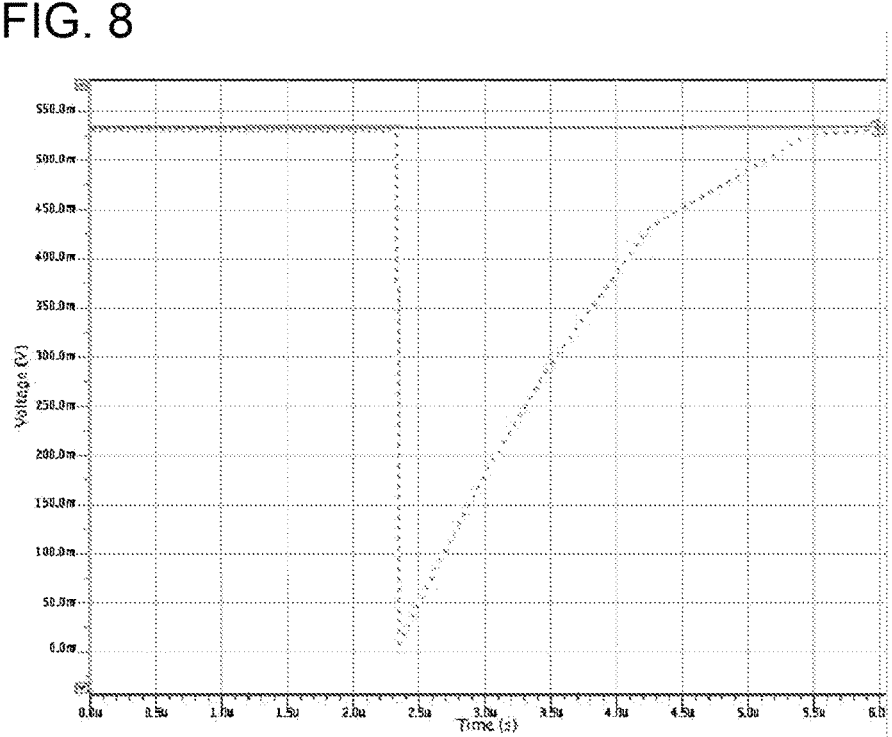
FIG. 8 is a graph that illustrates electrical quantities corresponding to the ultrasonic probe of FIG. 2 during transition between the first operating configuration and the second operating configuration.

FIG. 8 shows by way of example the voltage at the input 20a of the first amplification stage 20 during transition from the transmitting configuration to the receiving configuration in the presence (solid line) and in the absence (dashed line) of the precharge mechanism.

The precharge step may also be interrupted to contain power consumption. Furthermore, thanks to the control of the current IBC according to the precharge relation, the precharge voltage level that may be obtained on the intermediate node 36 is accurate. The precharge relation may then be selected in a flexible way to obtain the desired balance between rapidity of switching (higher precharge current IBC and shorter precharge time interval $\Delta T$) and reduction of consumption (lower precharge current IBC and longer precharge time interval $\Delta T$).

The delay of some nanoseconds caused by the slow transition of the low-voltage switches 28, 29 is in any case amply compatible with the switching times of the T/R selector 13 for sonographic investigation in near field. Against this altogether negligible delay, a considerable reduction of the charge injection and of the associated noise is obtained.

The solution described favors in particular the use of charge amplifiers in the first stage of the receiver circuit 14. This type of amplifier, in fact, may be advantageous from certain standpoints, but has low bias currents that would render the transition very slow, unless the consumption levels are sacrificed to a significant extent. The precharge of the intermediate node 36 enables speeding-up of the transition also with charge amplifiers at the first amplification stage.

Figure 9:
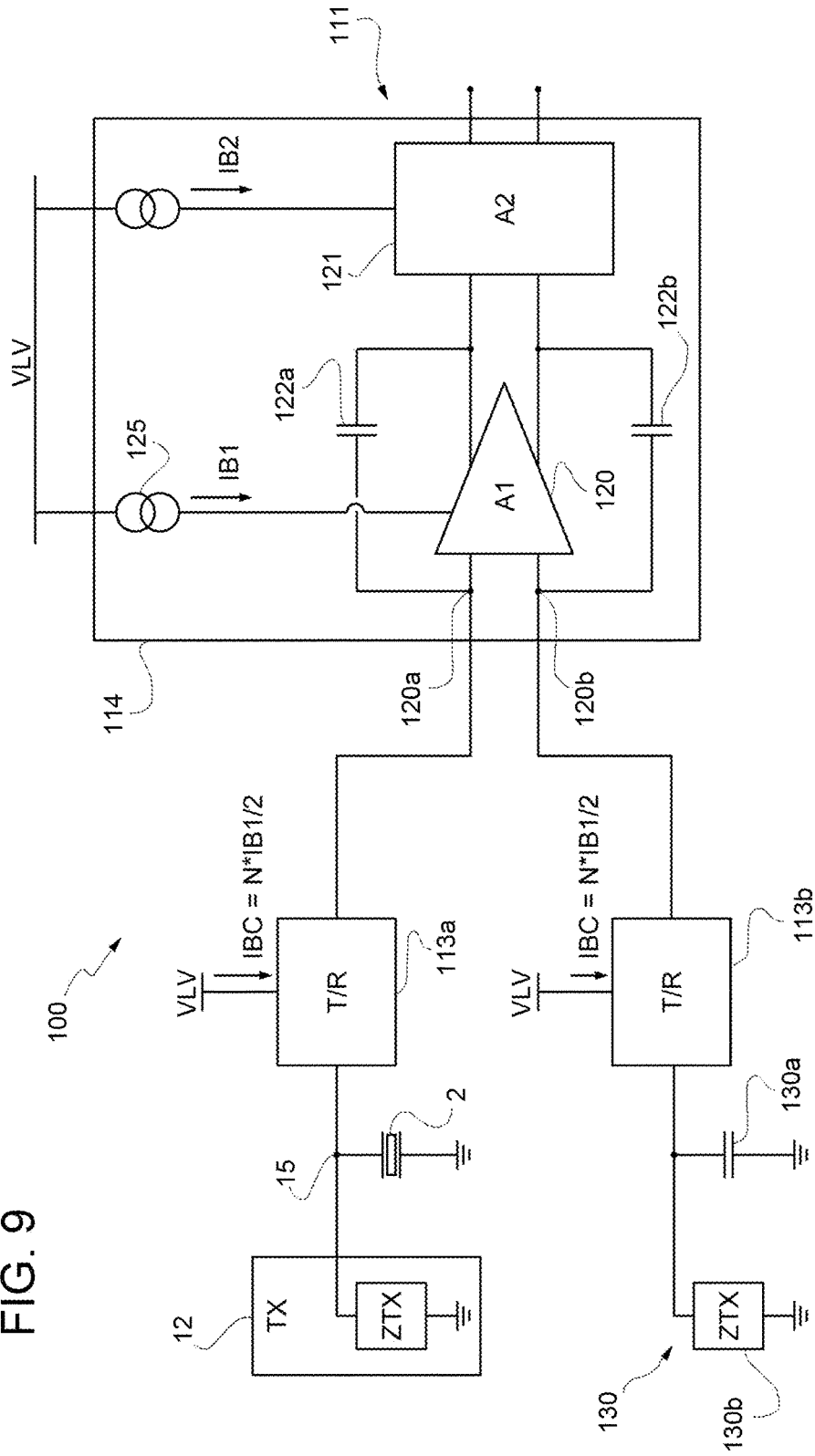
FIG. 9 is a block diagram of an ultrasonic probe according to an embodiment.

FIG. 9 illustrates another embodiment. In this case, an ultrasonic probe 100 (not illustrated entirely) comprises a plurality of transmit/receive channels 111 (just one of which is visible in FIG. 9). Each channel 111 comprises an ultrasonic transducer 2 and a pulse generator 12 of the types already described with reference to FIGS. 2-7. Furthermore, each channel 111 comprises a receiver circuit 114.

The receiver circuit 114 comprises an input amplification stage 120, which provides a gain contribution A1, and possible further amplification stages 121, which provide a further gain contribution A2.

In the embodiment described, the input amplification stage 120 is of a differential type in charge-amplifier configuration and has inputs 120a, 120b connected to respective outputs by respective capacitors 122a, 122b. Furthermore, one of the inputs, here the input 120a, are selectively connectable to the transducer 2 by a first T/R selector 113a; the other input of the input amplification stage 120 are selectively connectable to an impedance-matching stage 130 by a second T/R selector 113b. The input amplification stage 120 receives a bias current IB1 from a bias generator 125. For instance, if the input amplification stage 120 comprises a differential pair of transistors, each transistor of the pair uses a bias current equal to half the overall bias current IB1.

The first T/R selector 113a is substantially of the type already described with reference to FIG. 4. In particular, the first T/R selector 113a comprises a copy stage that has a structure substantially similar to that of the input amplification stage 120, but for a scale factor. For instance, if the input amplification stage 120 comprises a differential pair of transistors, the copy stage comprises a transistor in the same configuration with oversized aspect ratio or a plurality of identical transistors in parallel to one another and in the same configuration. Furthermore, in the precharge step, the T/R selector 113a absorbs a precharge current IBC equal to half the overall bias current IB1 of the input amplification stage 120.

The second T/R selector 113b has a structure identical to that of the first T/R selector 113a.

The impedance-matching stage 130 replicates the impedance upstream of the first T/R selector 115a. In one embodiment, the impedance-matching stage 130 comprises: a first component 130a of a capacitive type, which replicates the capacitance of the transducer 2; and a second component 130b, which replicates an output impedance ZTX of the pulse generator 12.

Finally, it is evident that modifications and variations may be made to the ultrasonic probe and to the method described herein, without thereby departing from the scope of the present disclosure.

Some embodiments may take the form of or include computer program products. For example, according to one embodiment there is provided a computer readable medium including a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some of the systems and/or modules and/or circuits and/or blocks may be implemented or provided in other manners, such as at least partially in firmware and/or hardware, including, but not limited to, one or more application-specific integrated circuits (ASICs), digital signal processors, discrete circuitry, logic gates, standard integrated circuits, state machines, look-up tables, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a low-voltage amplifier including an amplifier input and amplifier biasing circuitry configured to bias the amplifier; and
   a selection circuit configured to couple between the amplifier input and an ultrasonic transducer and including:
      a node;
      a first switch coupled between the node and the amplifier input; and
      node biasing circuitry coupled to the amplifier biasing circuitry and configured to, before the first switch couples the node to the amplifier input in a receive mode of operation, bias the node based on the biasing of the amplifier.

2. The device of claim 1 wherein,
   the amplifier-input biasing circuitry comprises a first current source,
   the node biasing circuitry comprises a second current source, and
   the first current source and the second current source are coupled together in a current-mirror configuration having a current mirror ratio.

3. The device of claim 2 wherein the selection circuitry comprises:
   a second switch coupled between the second current source and the node; and
   at least one transistor having a control terminal coupled to the node and conduction terminals configured to couple between the node and a reference voltage terminal.

4. The device of claim 3, comprising a high-voltage switch configured to couple between the node and the ultrasonic transducer.

5. The device of claim 4, comprising a diode coupled between the node and the reference voltage.

6. The device of claim 4, comprising a controller configured to control operation of the first, second and high-voltage switches.

7. The device of claim 6 wherein the controller is configured to control the second switch and the high voltage switch to, in operation, couple the second current source to the node for a pre-charge period before coupling the ultrasonic transducer to the node.

8. The device of claim 6, comprising a third switch coupled between a conduction terminal of the at least one transistor and the reference voltage terminal, wherein the controller is configured to, in operation, control the first and third switches to simultaneously disconnect the conduction terminal of the at least one transistor from the reference voltage terminal and couple the node to the amplifier input.

9. The device of claim 8 wherein the first and third switches comprise transistors and the controller is configured to apply ramp voltages to simultaneously disconnect the conduction terminal of the at least one transistor from the reference voltage terminal and couple the node to the amplifier input.

10. The device of claim 2 wherein:
    the amplifier comprises at least one first transistor having:
       a conduction terminal coupled to the first current source;
       a control terminal coupled to the amplifier input; and
       a first aspect ratio; and
    the selection circuit comprises at least one second transistor having:
       a conduction terminal configured to couple to the second current source;
       a control terminal coupled to the node; and
       a second aspect ratio, where the second aspect ratio is a multiple of the first aspect ratio and the multiple is based on the current mirror ratio.

11. The device of claim 2 wherein the current mirror ratio is greater than 1.

12. The device of claim 1 wherein the node biasing circuitry is configured to, before the first switch couples the node to the amplifier input in the receive mode of operation, bias the node to a bias voltage substantial equal to a biasing voltage of the amplifier.

13. The device of claim 1 wherein the amplifier has a charge amplifier configuration.

14. The device of claim 1 wherein the amplifier has a differential amplifier configuration having a second amplifier input, comprising:
    a second selection circuit configured to couple between the second amplifier input and an impedance representative of an impedance of the ultrasonic transducer and including:
       a second node;
       a switch coupled between the second node and the second amplifier input; and
       second node biasing circuitry coupled to the amplifier biasing circuitry and configured to, before the switch coupled between the second node and the second amplifier input couples the second node to the second amplifier input in the receive mode of operation, bias the second node based on the biasing of the amplifier.

15. A system, comprising:
    an ultrasonic transducer;
    a low-voltage amplifier including an amplifier input and amplifier biasing circuitry configured to bias the amplifier; and
    a selection circuit configured to couple between the amplifier input and the ultrasonic transducer, and including:
       a node;
       a first switch coupled between the node and the amplifier input; and
       node biasing circuitry coupled to the amplifier biasing circuitry and configured to, before the first switch couples the node to the amplifier input in a receive mode of operation, bias the node based on the biasing of the amplifier.

16. The system of claim 15 wherein,
    the amplifier-input biasing circuitry comprises a first current source,
    the node biasing circuitry comprises a second current source, and
    the first current source and the second current source are coupled together in a current-mirror configuration having a current mirror ratio.

17. The system of claim 16 wherein the selection circuit comprises:
    a second switch coupled between the second current source and the node; and
    at least one transistor having a control terminal coupled to the node and conduction terminals configured to couple between the node and a reference voltage terminal.

18. The system of claim 17, comprising a high-voltage switch configured to couple between the node and the ultrasonic transducer.

19. The system of claim 18, comprising a controller configured to control operation of the first, second and high-voltage switches.

20. The system of claim 15 wherein the amplifier has a differential amplifier configuration having a second amplifier input, comprising:
a second selection circuit configured to couple between the second amplifier input and an impedance representative of an impedance of the ultrasonic transducer and including:
a second node;
a switch coupled between the second node and the second amplifier input; and
second node biasing circuitry coupled to the amplifier biasing circuitry and configured to, before the switch coupled between the second node and the second amplifier input couples the second node to the second amplifier input in the receive mode of operation, bias the second node based on the biasing of the amplifier.

21. A method, comprising:
controlling a selector, the selector having an intermediate node, a high-voltage switch coupled between the intermediate node and an ultrasonic transducer, and a low-voltage switch coupled between the intermediate node and an input terminal of an amplification stage of an ultrasonic probe, to alternately couple and decouple the transducer and the amplification stage; and
precharging the intermediate node as a function of a bias voltage on the input terminal of the amplification stage before coupling the amplification stage and the transducer.

22. The method according to claim 21 wherein the precharging comprises bringing the intermediate node to a precharge voltage substantially equal to the bias voltage.

23. The method of claim 21, comprising starting the precharging before coupling the transducer to the intermediate node.

24. The method of claim 21 wherein the low voltage switch comprises a first transistor, comprising simultaneously:
applying a first ramp voltage to a second transistor to decouple the intermediate node from a reference voltage terminal; and
applying a second ramp voltage to the first transistor to couple the intermediate node to the input terminal of the amplification stage.

25. A non-transitory computer-readable medium having contents which configure a system to perform a method, the method comprising:
controlling a selector, the selector having an intermediate node, a high-voltage switch coupled between the intermediate node and an ultrasonic transducer, and a low-voltage switch coupled between the intermediate node and an input terminal of an amplification stage of an ultrasonic probe, to alternately couple and decouple the transducer and the amplification stage; and
precharging the intermediate node as a function of a bias voltage on the input terminal of the amplification stage before coupling the amplification stage and the transducer.

26. The medium of claim 25 wherein the precharging comprises bringing the intermediate node to a precharge voltage substantially equal to the bias voltage.

27. The medium of claim 25 wherein the method comprises starting the precharging before coupling the transducer to the intermediate node.

28. The medium of claim 25 wherein the method comprises simultaneously:
decoupling the intermediate node from a reference voltage terminal; and
coupling the intermediate node to the input terminal of the amplification stage.

* * * * *